US010376656B2

(12) United States Patent
Dyer et al.

(10) Patent No.: US 10,376,656 B2
(45) Date of Patent: Aug. 13, 2019

(54) SIDE-ANGLE DECAPPING OF PRE-FILLED SYRINGE

(71) Applicant: Portal Instruments, Inc., Cambridge, MA (US)

(72) Inventors: Robert J. Dyer, Concord, MA (US); Andrew Coats, Somerville, MA (US)

(73) Assignee: Portal Instruments, Inc., Cambridge, MA (US)

( * ) Notice: Subject to any disclaimer, the term of this patent is extended or adjusted under 35 U.S.C. 154(b) by 188 days.

(21) Appl. No.: 15/598,653

(22) Filed: May 18, 2017

(65) Prior Publication Data

US 2017/0333633 A1 Nov. 23, 2017

Related U.S. Application Data

(60) Provisional application No. 62/337,967, filed on May 18, 2016.

(51) Int. Cl.
| *A61M 5/24* | (2006.01) |
| *A61M 5/36* | (2006.01) |
| *A61M 5/32* | (2006.01) |
| *A61M 5/30* | (2006.01) |

(52) U.S. Cl.
CPC ............... *A61M 5/36* (2013.01); *A61M 5/24* (2013.01); *A61M 5/2466* (2013.01); *A61M 5/30* (2013.01); *A61M 5/3204* (2013.01)

(58) Field of Classification Search
CPC .......... A61M 5/3204; A61M 2005/206; A61M 2005/2496; A61M 5/24; A61M 5/36; A61M 5/2466; A61M 5/30
See application file for complete search history.

(56) References Cited

U.S. PATENT DOCUMENTS

| 2009/0270672 | A1* | 10/2009 | Fago | A61M 5/1785 |
| | | | | 600/5 |
| 2010/0185148 | A1* | 7/2010 | Gillespie, III | A61M 5/2033 |
| | | | | 604/110 |
| 2010/0312195 | A1* | 12/2010 | Johansen | A61M 5/2033 |
| | | | | 604/192 |
| 2012/0022499 | A1* | 1/2012 | Anderson | A61M 5/14248 |
| | | | | 604/506 |
| 2012/0035542 | A1* | 2/2012 | Pongprairochana | A61M 5/20 |
| | | | | 604/110 |
| 2015/0290392 | A1* | 10/2015 | Henderson | A61M 5/20 |
| | | | | 604/111 |
| 2015/0297833 | A1* | 10/2015 | Henderson | A61M 5/2033 |
| | | | | 604/135 |
| 2016/0354553 | A1* | 12/2016 | Anderson | A61M 5/3298 |
| 2018/0304014 | A1* | 10/2018 | Knudsen | A61M 5/1454 |

FOREIGN PATENT DOCUMENTS

WO WO-2017089265 A1 * 6/2017 ............. A61M 5/20

\* cited by examiner

*Primary Examiner* — William R Carpenter
(74) *Attorney, Agent, or Firm* — Occhiuti & Rohlicek LLP

(57) ABSTRACT

An injector cartridge is configured for sterile storage and transfer of a fluid in a pre-filled syringe. The injector cartridge includes a first housing section and a second housing section and is configured to move the pre-filled syringe from a sterile storage position to a fluid transfer position upon linear displacement of the first housing section relative to the second housing section.

20 Claims, 11 Drawing Sheets

Preparing a injector cartridge for use, the injector cartridge having a first section, a second section slidably coupled to the first section permitting sliding of the second section in a sliding direction relative to the first section, and an elongated liquid-filled capsule having a first end a second end opposite the first end, the capsule pivotably coupled at the first end to the second section and mechanically biased to align the capsule with the sliding direction, and having an opening at the second end, the preparing including:

269

Accepting the injector cartridge in a first configuration in which the capsule is offset in direction from the sliding direction, and the second end of the capsule is engaged in the first section of the housing such that the opening at the second end of the capsule is closed.

270

Sliding the second section relative to the first section to cause the injector cartridge to transform from the first configuration to a second configuration in which the capsule is aligned with the sliding direction and the second end of the capsule is free of the second section.

272

Sliding the second section relative to the first section to cause the injector cartridge to transform from the second configuration to a third configuration different that the first configuration in which the capsule is aligned with the sliding direction and the second end of the capsule is engaged in the first section such that the opening at the second end of the capsule is open permitting transfer of fluid from the capsule.

SIDE-ANGLE DECAPPING OF PRE-FILLED SYRINGE

CROSS-REFERENCE TO RELATED APPLICATIONS

This application claims the priority of U.S. Provisional Application No. 62/337,967 filed on May 18, 2016. The contents of which is incorporated herein by reference in its entirety.

BACKGROUND

This invention relates to a pre-filled syringe (PFS) fluid transfer injector cartridge.

The skin of organisms such as humans serves as a protective barrier that, among other functions, prevents pathogens from entering the body and prevents or regulates fluids such as blood and water from exiting the body. In the field of modern medicine, there is often a need to deliver injectates such as drugs through the skin and into the bloodstream or tissue of patients. Traditionally, this delivery of liquids into a patient's body is accomplished by having a technician insert a needle through the patient's skin and into an area inside of the patient's body where the liquid can enter the patient's blood stream.

SUMMARY

Some injection devices are configured to receive an injector cartridge that includes an injectate. In general, injector cartridges are configured to be attached to the injection device prior to injection, and to be removed from the injection device after injection (and possibly discarded). Some injector cartridges include an injection chamber that is pre-filled with an injectate. However, it is often the case that, when initially released, drugs and other injectates cannot be stored and sold in injection chambers of injector cartridges. For example, when new injection devices are initially released, drugs and other injectates may not yet be available in cartridges that are compatible with the new injection devices. Furthermore, when drugs are initially released, they may only be stored and sold in syringe form (e.g., due to regulatory issues and/or drug stability and shelf life issues). Thus, there is a need for an injector cartridge that is compatible with an injection device and is configured to receive a pre-filled syringe and transfer injectate from the pre-filled syringe to an injection chamber of the injector cartridge.

In a general aspect, an injector cartridge for sterile storage and transfer of a fluid in a pre-filled syringe having a first end and a second end with a needle covered by a removable cap includes an attachment member configured to pivotally constrain the first end of the pre-filled syringe, a first support to axially retain the cap on the second end of the pre-filled syringe, a second support to receive and axially retain the needle in a deployed position when the cap is removed from the second end, a spring positioned to rotationally bias the second end of the pre-filled syringe from the first support toward the second support around a pivot formed at the attachment member, a first housing section securing the first support and the second support in a fixed relationship to one another, and a second housing section coupled to the attachment member, the second housing section coupled in a sliding relationship to the first housing section. When the pre-filled syringe is placed between the attachment member and the first support, the syringe is decapped by the first support and rotated by the spring into alignment with the second support upon a first linear displacement of the second housing section away from the first housing section, and wherein the needle of the syringe is inserted into the second support by a subsequent linear displacement of the second housing section toward the first housing section.

Aspects may include one or more of the following features.

The injector cartridge may include a fluid dispensing chamber, where the deployed position fluidly couples the pre-filled syringe to the fluid dispensing chamber. The injector cartridge may include a channel extending between the second support and the fluid dispensing chamber for fluidly coupling the fluid dispensing chamber and the pre-filled syringe. The channel may include a bung and the bung is punctured by the needle of the pre-filled syringe such that the pre-filled syringe and the fluid dispensing chamber are coupled. The deployed position may expose the needle for injection of the fluid from the pre-filled syringe into target tissue. The attachment member may include a snap-fit connection configured pivotally constrain the first end of the pre-filled syringe. The first housing section may be configured to slide into the second housing section. The second housing section may be configured to slide into the first housing section.

The injector cartridge may include a nozzle disposed in a first wall at a distal end of the first housing section, the nozzle being in fluid communication with the fluid dispensing chamber, a first opening disposed in a second wall at a proximal end of the second housing section and coaxially aligned with the fluid dispensing chamber, and a second opening disposed in the second wall. The injector cartridge may include the pre-filled syringe, wherein the pre-filled syringe includes a syringe bore which, in the deployed position of the syringe, extends in a direction such that the syringe bore is coaxially aligned with the second opening. The injector cartridge may include a removable seal covering the nozzle. The injector cartridge may include the pre-filled syringe.

In another general aspect, an injector cartridge includes a first section and a second section slidably coupled to the first section permitting sliding of the second section in a sliding direction relative to the first section. The injector cartridge is configured to receive an elongated liquid-filled capsule having a first end and a second end opposite the first end, such that the capsule is pivotably coupled at the first end to the second section and mechanically biased to align the capsule with the sliding direction, and having an opening at the second end. The injector cartridge is further configured such that sliding the second section relative to the first section causes the injector cartridge to transform from a first configuration to a second configuration, and then sliding the first section relative to the second section causes the injector cartridge to transform from the second configuration to a third configuration different than the first configuration, and in the first configuration of the injector cartridge, the injector cartridge causes the capsule to be angularly offset in direction from the sliding direction, and the second end of the capsule to be engaged in the first section of the housing such that the opening at the second end of the capsule is closed. In the second configuration of the injector cartridge, the injector cartridge causes the capsule to be aligned with the sliding direction and the second end of the capsule to be free of the first section. In the third configuration of the injector cartridge, the injector cartridge causes the capsule to be aligned with the sliding direction and the second end of the capsule to be engaged in the first section such that the opening at the second end of the capsule permits transfer of fluid from the capsule.

Aspects may include one or more of the following features.

The injector cartridge may include an energy storage element configured to be disposed between an inner surface of the second section and an outer surface of the capsule, the energy storage element being configured to mechanically bias the capsule toward a position that is aligned with the sliding direction. The energy storage element may include a spring. The spring may have a first degree of compression in the first configuration and has a second degree of compression, less than the first degree of compression, in the second configuration and the third configuration. The first section may include a cap and the injector cartridge may be configured to cause the second end of the capsule to be disposed in the cap in the first configuration, and to be removed from the cap in the second configuration and the third configuration. The injector cartridge may include a fluid transfer apparatus and a chamber including a chamber bore extending in a direction substantially parallel to the sliding direction, the fluid transfer apparatus including a fluid transfer channel in fluid communication with the chamber bore, the fluid transfer channel having a bung disposed therein.

In the third configuration, the injector cartridge may be configured to cause a portion of the second end of the capsule to extend through the bung and establish fluid communication between the capsule and the fluid transfer channel. The injector cartridge may include a nozzle disposed in a first wall at a distal end of the first section of the housing, the nozzle being in fluid communication with the chamber bore, a first opening disposed in a second wall at a proximal end of the second section of the housing and coaxially aligned with the chamber bore, and a second opening disposed in the second wall. The injector cartridge may include the capsule, wherein the capsule includes a capsule bore which, in the third configuration, extends in a direction substantially parallel to the sliding direction such that the capsule bore is coaxially aligned with the second opening. The injector cartridge may include the capsule. The capsule may be a syringe.

The first section may be shaped and sized to fit within the second section. The second section may be shaped and sized to fit within the first section. The second section may include a chamber for pivotably coupling the first end of the capsule to the second section, the chamber being configured to receive and contain a flange disposed at the first end of the capsule and including an opening configured to receive an elongate body of the capsule with the elongate body extending through the opening in the chamber. The attachment member may be formed as a snap-fit connection configured to receive and contain the flange.

In another general aspect, a method for preparing a injector cartridge for use, the injector cartridge having a first section, a second section slidably coupled to the first section permitting sliding of the second section in a sliding direction relative to the first section, and an elongated liquid-filled capsule having a first end a second end opposite the first end, the capsule pivotably coupled at the first end to the second section and mechanically biased to align the capsule with the sliding direction, and having an opening at the second end, includes accepting the injector cartridge in a first configuration in which the capsule is offset in direction from the sliding direction, and the second end of the capsule is engaged in the first section of the housing such that the opening at the second end of the capsule is closed, sliding the second section relative to the first section to cause the injector cartridge to transform from the first configuration to a second configuration in which the capsule is aligned with the sliding direction and the second end of the capsule is free of the second section, and sliding the second section relative to the first section to cause the injector cartridge to transform from the second configuration to a third configuration different that the first configuration in which the capsule is aligned with the sliding direction and the second end of the capsule is engaged in the first section such that the opening at the second end of the capsule is open permitting transfer of fluid from the capsule.

Aspects may have one or more of the following advantages.

Among other advantages, aspects may allow for needle-free transdermal injection of drugs when the drugs are only available in syringe form.

Aspects of the invention facilitate sterile transfer of injectate from a syringe to an injection chamber of a needle-free transdermal injector cartridge.

Aspects of the invention eliminate needle-prick risk for a person performing a transfer of injectate from a syringe to an injection chamber of a needle-free transdermal injector cartridge.

Aspects of the invention facilitate a simple, foolproof method for transferring injectate from a syringe to an injection chamber of a needle-free transdermal injector cartridge that requires very little hand-eye coordination and stability of movement.

Aspects of the invention maintain the syringe, including the needle, within an injector cartridge such that contamination of the syringe (e.g., by human contact with the syringe) is prevented.

Aspects of the invention obviate the need for removal of a cap by a user of the cartridge, thereby minimizing a number of disposable and loose parts.

DESCRIPTION OF DRAWINGS

FIG. 2a is a block diagram showing a series of steps for operating the pre-filled syringe fluid transfer injector cartridge of FIG. 2.

DESCRIPTION

Figure 1:
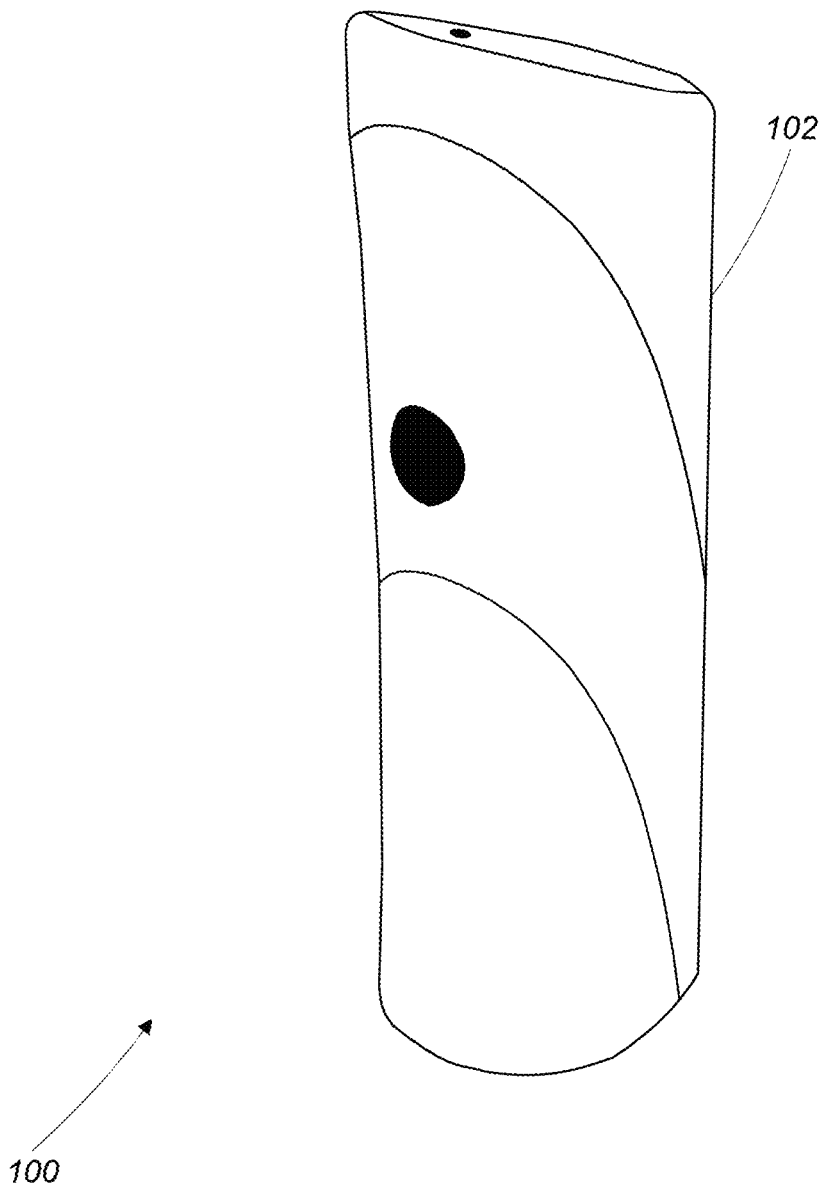
FIG. 1 is a needle-free transdermal injection device.

Referring to FIG. 1, a needle-free transdermal injection device 100 includes an injector mechanism 102 with a fluid transfer injector cartridge (not shown) disposed therein.

Very generally, the injector mechanism 102 operates the fluid transfer injector cartridge to eject an injectate from a chamber within the fluid transfer injector cartridge and to deliver the ejected injectate through the skin and into the bloodstream of a patient.

1 Pre-Filled Syringe Fluid Transfer Device

Figure 2:
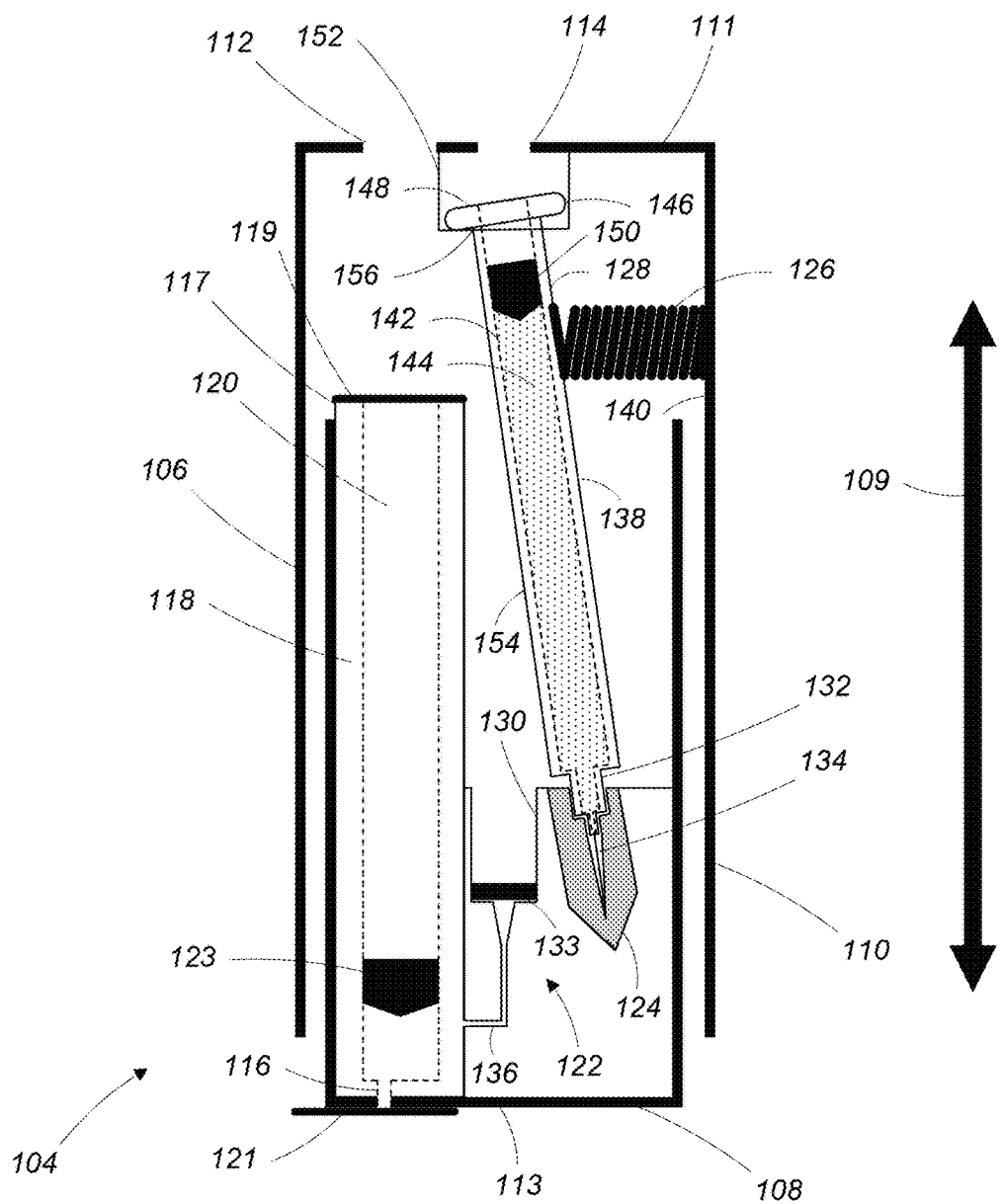
FIG. 2 is a pre-filled syringe fluid transfer injector cartridge in a storage configuration.

Referring to FIG. 2, an embodiment of a pre-filled syringe fluid transfer injector cartridge 104 is configurable into a number of different configurations including a first, storage configuration for sterile storage of a pre-filled syringe, a second, alignment configuration for uncapping and alignment of the pre-filled syringe, and a third, fluid transfer configuration for transfer of injectate from the pre-filled syringe and into an injection chamber.

The pre-filled syringe fluid transfer injector cartridge 104 includes a housing 106 including a first housing section 108 that is slidably coupled to a second housing section 110. The first housing section 108 is sized and shaped to fit within the second housing section 110 such that the first housing section 108 and the second housing section 110 can slide relative to one another, in a telescoping manner, in a sliding direction 109. In other examples, the second housing section 110 is sized and shaped to fit within the first housing section 108 such that the first housing section 108 and the second housing section 110 can slide relative to one another, in a telescoping manner, in the sliding direction 109.

The second housing section 110 includes an injection plunger opening 112 and a syringe plunger opening 114 at its proximal end 111. As is described in detail below, the injection plunger opening 112 and the fluid transfer plunger opening 114 are configured to receive an injection plunger and a fluid transfer plunger (or pin), respectively, of the injector mechanism 102. The first housing section 108 includes an injection nozzle 116 at its distal end 113. In some examples, the injection nozzle 116 is integrally formed with the first housing section 108. In other examples, the injection nozzle 116 is formed as part of an injection chamber 118 (which may be removable). The distal end of the first housing section 113 includes a removable seal 121 covering the injection nozzle 116 for preventing injectate from inadvertently leaking from the injection nozzle 116 and for preventing debris from entering the injection nozzle 116. During an injection operation, a jet of injectate is ejected from the fluid transfer injector cartridge 104 through the injection nozzle 116.

The housing 106 includes the injection chamber 118 coupled to the first housing section 108, a fluid transfer apparatus 122 coupled to the first housing section 108, a syringe cap 124 coupled to the first housing section 108, an energy storage element 126 coupled to the first housing section 108, and a syringe 128 pivotably coupled to the proximal end 111 of the second housing section 110. A proximal end 117 of the injection chamber 118 includes a vented seal 119 covering an opening into an injection chamber bore 120 for receiving injectate. The injection chamber bore 120 is coaxially aligned with the injection plunger opening 112 and is in fluid communication with the injection nozzle 116. A injection stopper 123 is disposed in the injection chamber bore 120.

The fluid transfer apparatus 122 includes a syringe chamber 130 for receiving a distal end 132 of the syringe 128, including a needle 134 of the syringe 128. A bung 133 is disposed in the syringe chamber 130 and separates, in a liquid-tight manner, the syringe chamber 130 of the fluid transfer apparatus 122 from a fluid transfer channel 136 that is in fluid communication with the bore 120 of the injection chamber 118.

In some examples, the first housing section 108 includes one or more clips or gripping features (e.g., snap-fit features) which interact with the syringe cap 124 to receive and retain the cap 124. The syringe cap 124 is configured to receive the distal end 132 of the syringe 128 to maintain sterility of the distal end 132 of the syringe 128.

The energy storage element 126 (e.g., a spring or a flexure) is disposed between an outer surface of a sidewall 138 of the syringe 128 and an inner surface of a sidewall 140 of the second housing section 110. In some examples, the energy storage element 126 applies a force to the outer surface of the sidewall 138 of the syringe 128 in a direction substantially perpendicular to the sliding direction 109.

The syringe 128 includes the needle 134 at its distal end 132, a syringe bore 142 for receiving injectate 144, and a flange 146 disposed at its proximal end 148. A stopper 150 is disposed in the syringe bore 142 and is configured to be moved along a length of the syringe 128 to force the injectate 144 out of the syringe 128 through the needle 134.

The proximal end 148 of the syringe 128 is pivotably held in place at the proximal end 111 of the second housing section 110 by an attachment member 152. In some examples, the attachment member 152 is a chamber that includes a through hole 156 with an inner diameter that is larger than an outer diameter of the main body 154 of the syringe 128 but is smaller than an outer diameter of the flange 146 of the syringe 128. With the syringe body 154 extending through the through hole 156, the flange 146 of the syringe 128 is held captive within the attachment member 152 due to the relatively larger outer diameter of the flange 146 preventing the flange 146 from passing through the through hole 156 which has a relatively smaller inner diameter.

The inner diameter of the through hole 156 is sufficiently large to allow the syringe 128 to move and pivot relative to the attachment member 152. The maximum range of movement and the maximum pivot angle is defined by dimensions of the syringe 128 (e.g., the outer diameters of the flange 146 and the main body 154) and the dimensions of the attachment member 152 (e.g., the inner diameter of the through hole 156). It is noted that the through hole 156 need not be a circular hole but can be of any sized and shape that pivotably holds the syringe 128 in place at the proximal end of the second housing section 110.

In other examples, the attachment member 152 includes clips and/or snap-fit features for receiving and interacting with the flange 146 at the proximal end 148 of the syringe 128 to pivotably hold the syringe 128. In yet other examples, the attachment member 152 is a partially enclosed chamber that is configured to receive a portion of the flange 146 at the proximal end 148 of the syringe 128 (e.g., the chamber can have a semi-circular shape configured to receive and pivotably hold half of the flange 146 at the proximal end 148 of the syringe 128).

Referring to FIG. 2a, a method for preparing an injector cartridge for use includes a number of steps. The method includes providing an injector cartridge (step 269) having a first section, a second section slidably coupled to the first section permitting sliding of the second section in a sliding direction relative to the first section. The injector cartridge also includes an elongated liquid-filled capsule. The elongated liquid filled capsule has a first end a second end opposite the first end and is pivotably coupled at the first end to the second section and mechanically biased to align the capsule with the sliding direction, and has an opening at the second end.

The injector cartridge is accepted in a first configuration in which the capsule is offset in direction from the sliding direction, and the second end of the capsule is engaged in the first section of the housing such that the opening at the second end of the capsule is closed (step 270).

The second section is slid relative to the first section to cause the injector cartridge to transform from the first configuration to a second configuration in which the capsule is aligned with the sliding direction and the second end of the capsule is free of the second section (step 272).

The second section is slid relative to the first section to cause the injector cartridge to transform from the second configuration to a third configuration different that the first configuration in which the capsule is aligned with the sliding direction and the second end of the capsule is engaged in the first section such that the opening at the second end of the capsule is open permitting transfer of fluid from the capsule (step 274).

The steps shown in FIG. 2a are described in greater detail below.

1.1 Storage Configuration

Referring again to FIG. 2, the pre-filled syringe fluid transfer injector cartridge 104 is shown in the first, storage configuration with the proximal end 148 of the syringe disposed in the attachment member 152. At least a portion of the flange 146 is engaged with an inner surface of the attachment member 152 such that the proximal end 148 of the syringe 128 is contained within the attachment member 152.

The syringe 128 is pivoted such that it extends at an angle relative to the sliding direction 109 with its distal end 132 disposed in the syringe cap 124. With the distal end 132 of the syringe 128 disposed in the syringe cap 124, the energy storage element 126 is prevented from displacing the syringe 128.

1.2 Aligned Configuration

Figure 3:
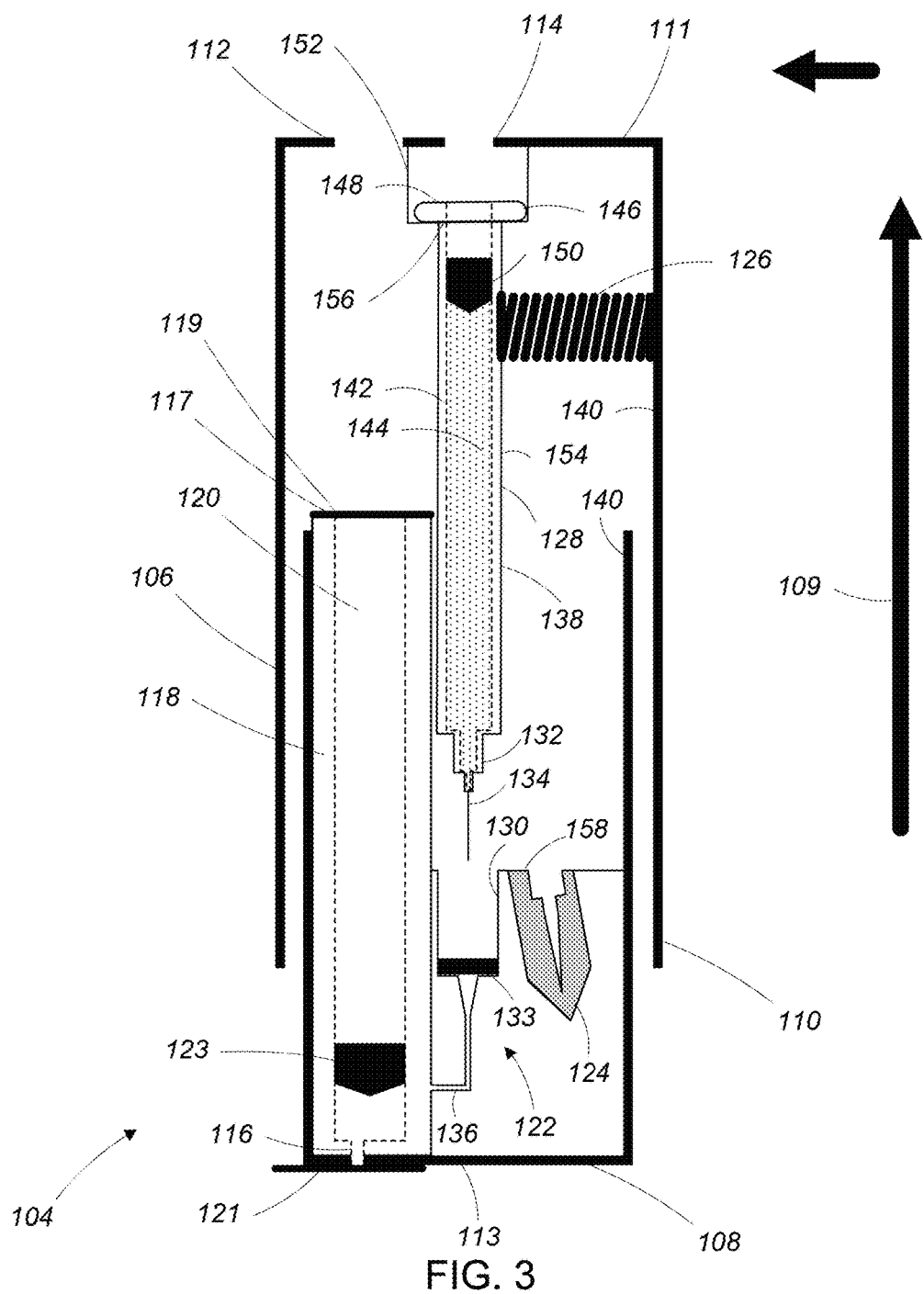
FIG. 3 is the pre-filled syringe fluid transfer injector cartridge of FIG. 2 in an aligned configuration.

Referring to FIG. 3, to prepare for fluid transfer of the injectate, the pre-filled syringe fluid transfer injector cartridge 104 is moved to a second, aligned configuration. To move the pre-filled syringe fluid transfer injector cartridge 104 from the first, storage configuration to the second, aligned configuration, the first housing section 108 and the second housing section 110 are caused to move relative to one another in the sliding direction 109 such that the proximal end 111 of the second housing portion 110 is moved in a direction away from the distal end 113 of the first housing portion 108.

Since the syringe cap 124 is coupled to the first housing portion 108 and the syringe 128 is coupled to the second housing portion 110, the movement of the distal end 113 of the first housing portion 108 away from the proximal end 111 of the second housing portion 110 causes removal of the distal end 132 of the syringe 128 from the syringe cap 124. Once the needle 134 of the syringe 128 is fully removed from the syringe cap 124 (i.e., the needle 134 is clear of a proximal end 158 of the cap 124), the force applied to the outer surface of the sidewall 138 of the syringe 128 by the energy storage element 126 causes the syringe 128 to pivot about the attachment member 152 such that the syringe is brought into alignment with the fluid transfer apparatus 122, extends substantially parallel to the sliding direction 109, and the syringe bore 142 is coaxially aligned with the fluid transfer plunger opening 114.

In some examples, the syringe 128 is maintained in the aligned configuration by the energy storage element 126 continuing to apply force to the outer surface of the sidewall 138 of the syringe 128 such that the syringe 126 is held between the energy storage element 126 and an outer surface of the injection chamber 118.

1.3 Fluid Transfer Configuration

Figure 4:
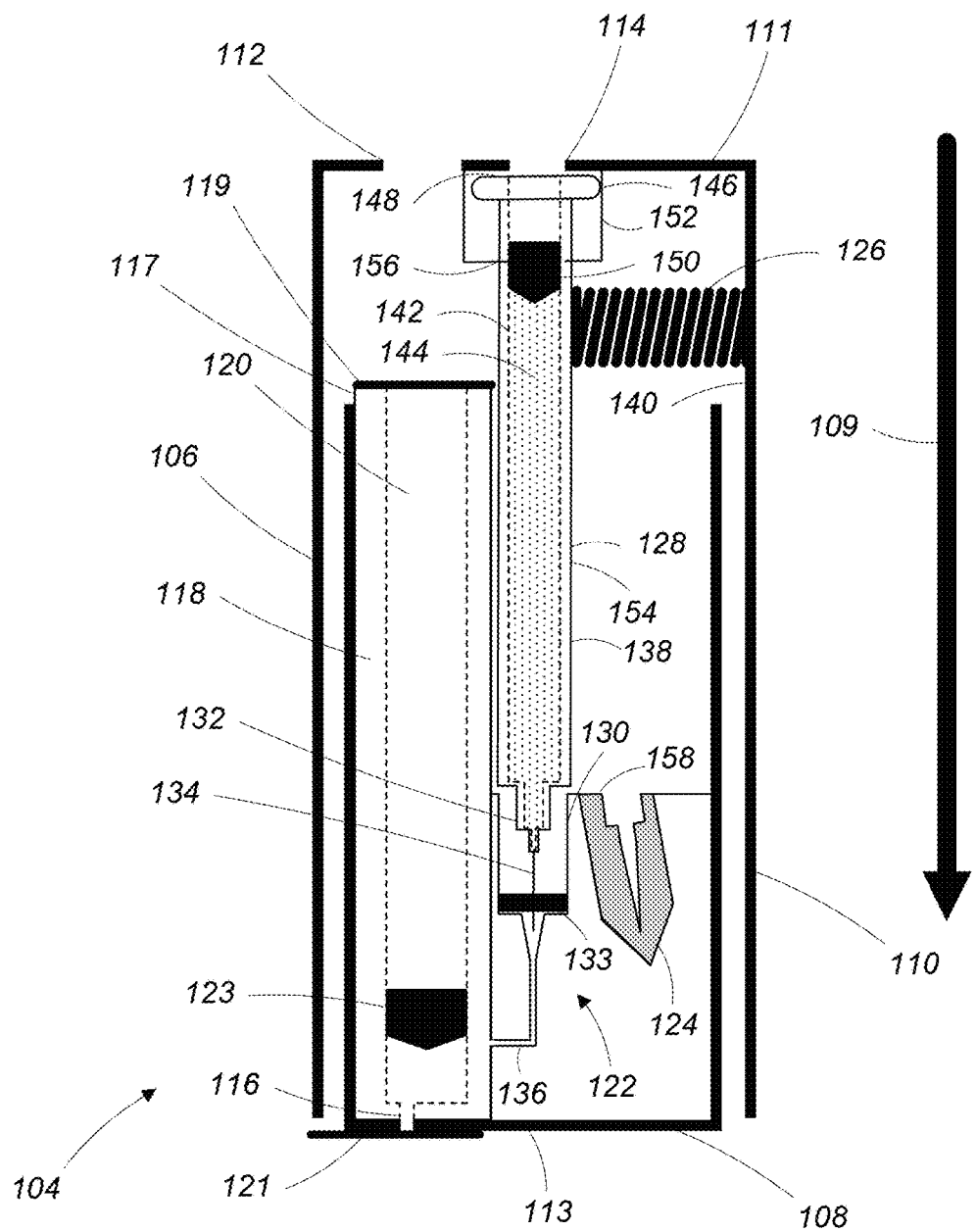
FIG. 4 is the pre-filled syringe fluid transfer injector cartridge of FIG. 2 in a fluid transfer configuration.

Referring to FIG. 4, after the pre-filled syringe fluid transfer injector cartridge 104 is moved to the second, aligned configuration, the pre-filled syringe fluid transfer injector cartridge 104 is moved to the third, fluid transfer configuration. To move the pre-filled syringe fluid transfer injector cartridge 104 from the second, aligned configuration to the third, fluid transfer configuration, the first housing section 108 and the second housing section 110 are caused to move relative to one another in the sliding direction 109 such that the proximal end 111 of the second housing section 110 is moved in a direction toward the distal end 113 of the first housing portion 108. As the first housing section 108 and the second housing section 110 move relative to one another, the distal end 148 of the syringe 128 makes contact with the distal end 111 of the second housing section 110. The first housing section 108 and the second housing section 110 continue move relative to one another, causing the syringe 128 to move in the sliding direction 109 toward the proximal end of the first housing section 108 until the distal end 132 of the syringe 128 enters the syringe chamber 130 of the fluid transfer apparatus 122 and the needle 134 of the syringe 128 punctures the bung 133.

2 Fluid Transfer and Injection

Figure 5:
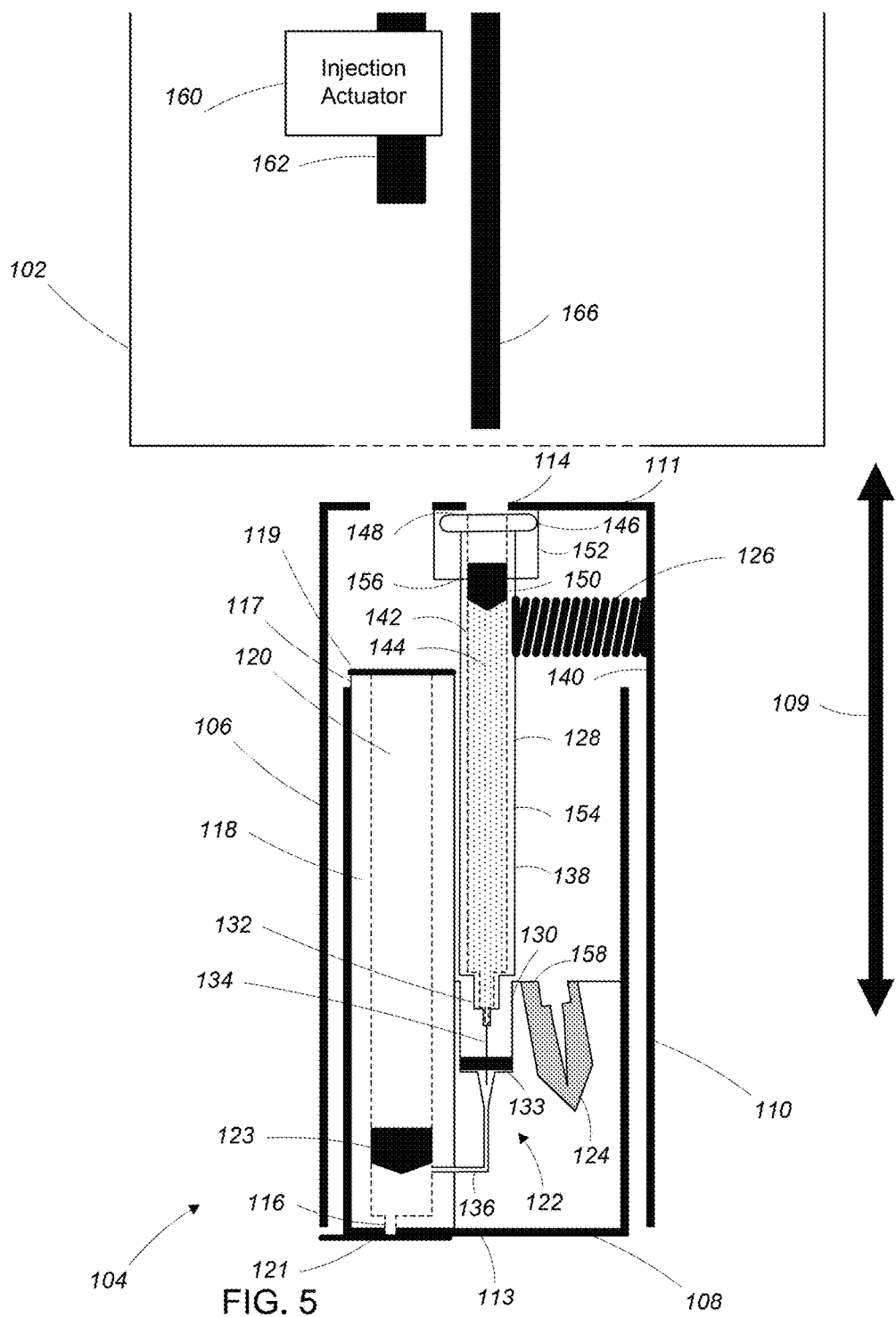
FIG. 5 is the pre-filled syringe fluid transfer injector cartridge of FIG. 2 attached to an injector mechanism.

Referring to FIG. 5, with the pre-filled syringe fluid transfer injector cartridge 104 in the third, fluid transfer configuration, the pre-filled syringe fluid transfer injector cartridge 104 is prepared for insertion into the injector mechanism 102. The injector mechanism 102 includes an injection actuator 160 for driving an injection plunger 162 and a static fluid transfer plunger 166.

Just prior to insertion of the pre-filled syringe fluid transfer injector cartridge 104 into the injector mechanism 102, the injection plunger 162 is coaxially aligned with the injection plunger opening 112 and the injection chamber bore 120. The fluid transfer plunger 166 is coaxially aligned with the fluid transfer plunger opening 114 and the syringe bore 142.

2.1 Fluid Transfer Phase

Figure 6:
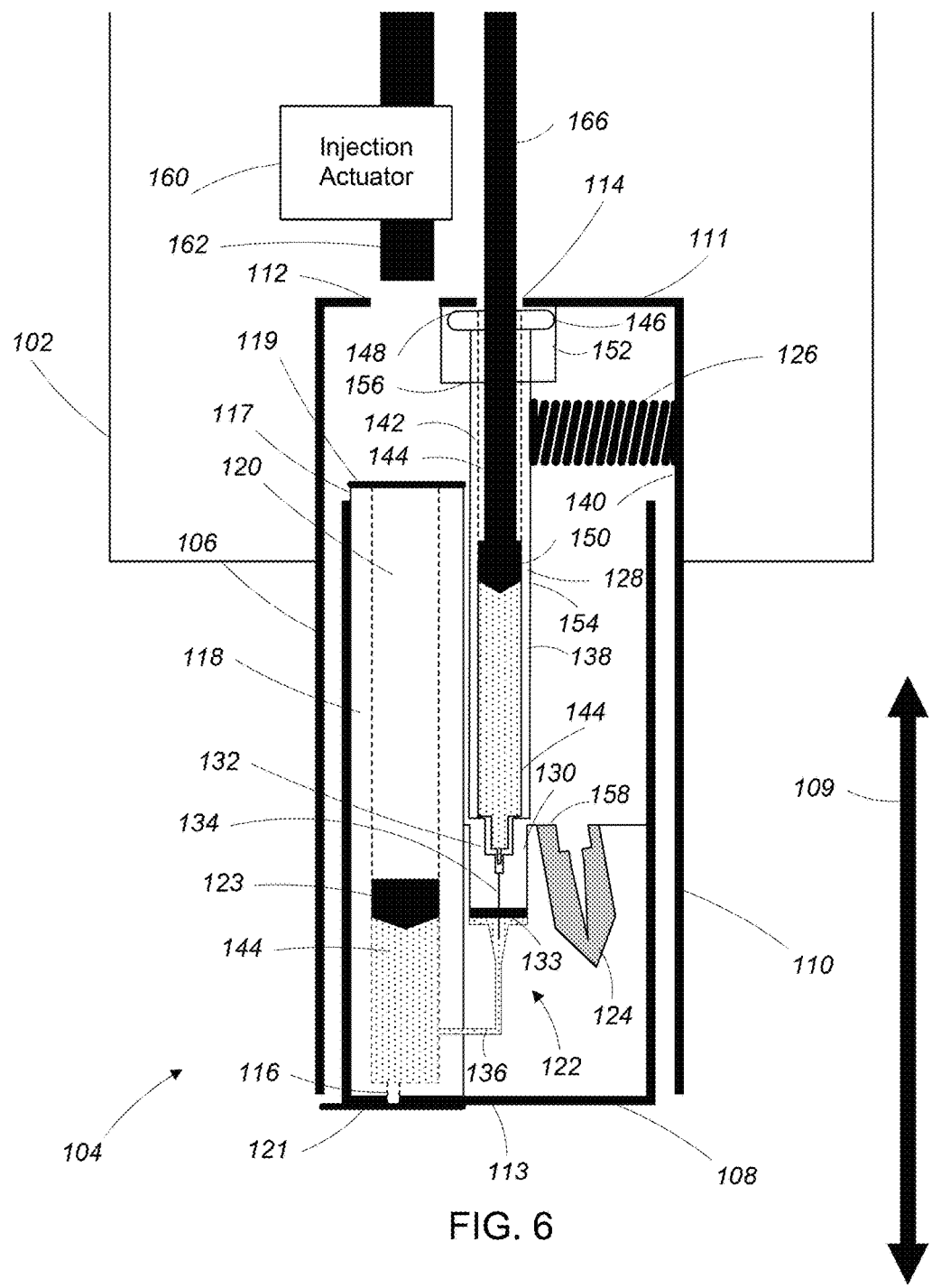
FIG. 6 shows a fluid transfer operation for the attached pre-filled syringe fluid transfer injector cartridge of FIG. 5.

Referring to FIG. 6, with the pre-filled syringe fluid transfer injector cartridge 104 properly aligned with the injector mechanism 102, the pre-filled syringe fluid transfer injector cartridge 104 is inserted into the injector mechanism 102 to commence the fluid transfer phase. In the fluid transfer phase, the injector mechanism 102 transfers a predetermined amount (i.e., a dose) of injectate from the syringe 128 into the injection bore 120 of the injection chamber 118. To do so, during insertion of the pre-filled syringe fluid transfer injector cartridge 104 into the injector mechanism 102, the static fluid transfer plunger 166 is forced through the fluid transfer plunger opening 114 and into the syringe bore 142. The fluid transfer plunger 166 moves through the syringe bore 140 and, at some point, encounters the stopper 150 and begins pushing the stopper 150 through the syringe bore 142.

As the stopper 150 is moved through the syringe bore 142, injectate 144 is expelled from the distal end 132 of the syringe 128 through the needle 134. Since the needle 134 has punctured the bung 133, the injectate 144 emerges from the needle 134 in the fluid transfer channel 136. The injectate 144 is forced through the fluid transfer channel 136 and into the injection bore 120 of the injection chamber 118. As fluid enters the injection bore 120 of the injection chamber 118, the injection stopper 123 moves in a direction toward the proximal end 117 of the injection chamber 118. As the injection stopper 123 moves through the injection bore 120, any gas in the injection bore 120 is forced out of the injection bore 120 through the vented seal 119. The fluid transfer phase ends when the pre-filled syringe fluid transfer injector cartridge 104 is fully inserted into the injection mechanism 102 and the predetermined amount of injectate is transferred from the syringe 128 into the injection bore 120 of the injection chamber 118.

In other embodiments, the fluid transfer plunger 166 is movable and is moved into and through the syringe bore 142 by a fluid transfer actuator (e.g., a linear actuator).

2.2 Injection Phase

Figure 7:
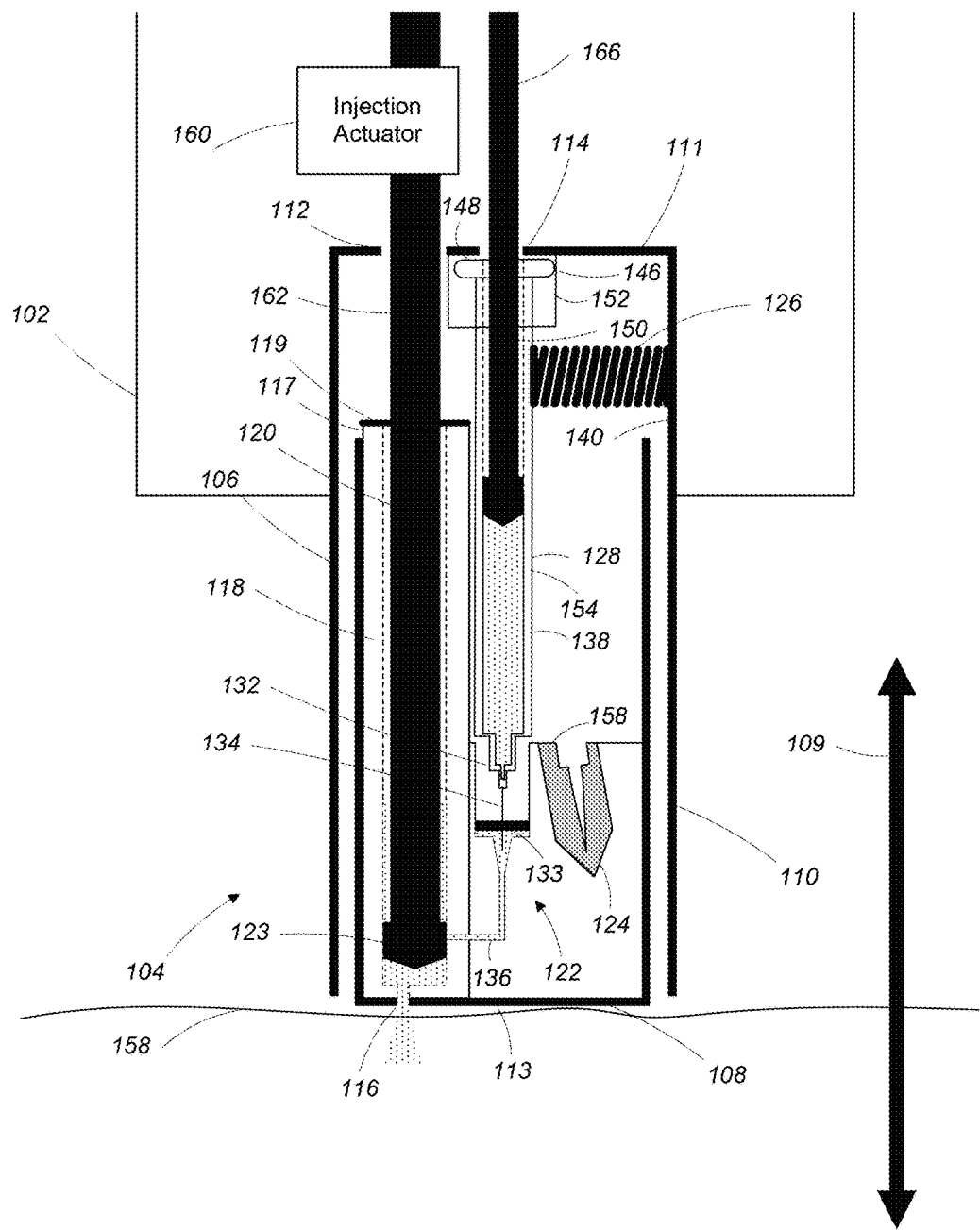
FIG. 7 shows an injection operation for the attached pre-filled syringe fluid transfer injector cartridge of FIG. 5.

Referring to FIG. 7, with the predetermined amount of injectate transferred into the injection bore 120 of the injection chamber, the injector mechanism 102 commences the injection phase. In the injection phase, the injector mechanism 102 causes a high pressure, narrow jet of injectate 144 to be expelled from the injection bore 120 through the injection nozzle 116. To do so, the injection actuator 160 causes the injection plunger 162 to move in a direction from the proximal end 111 of the second housing section 110 toward the distal end of the first housing section 108. The injection plunger 162 perforates the vented seal 119 and then enters the injection bore 120. As the injection plunger 162 moves through the injection bore 120, the injectate 144 present in the injection bore 120 is forced out of the injection bore 120 through the injection nozzle 116 and through the subject's skin 158.

In some examples, the removable seal 121 is removed from the distal end 113 of the first housing portion 108 prior to moving the pre-filled syringe fluid transfer injector cartridge 104 into the injection configuration. In other examples, the removable seal 121 is left on the distal end 113 of the first housing portion 108 and the injectate 144 perforates the removable seal 121 when the injectate 144 is forced out of the injection bore 120 through the injection nozzle 116.

3 Pre-Filled Syringe Auto-Injector

Figure 8:
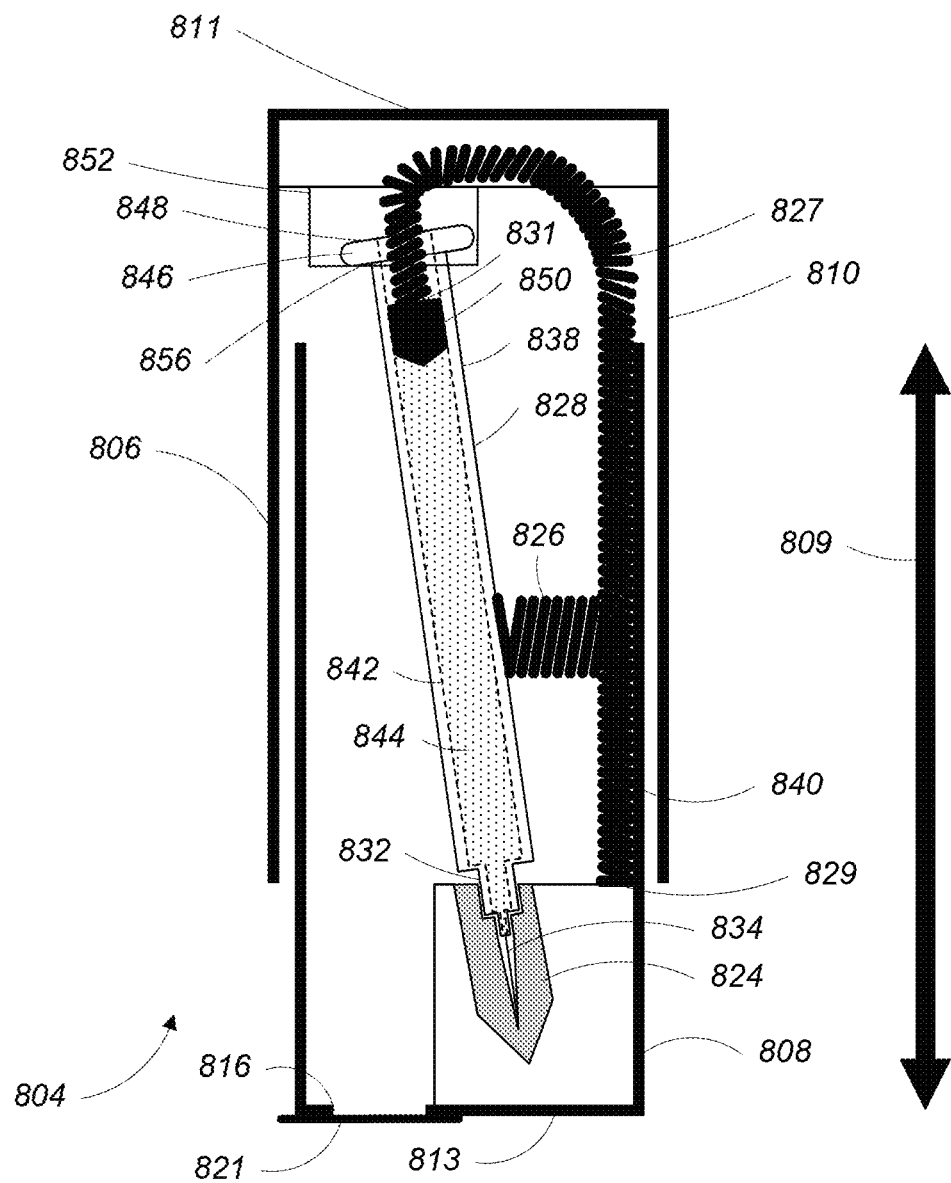
FIG. 8 is a pre-filled syringe auto-injector in a storage configuration.

Referring to FIG. 8, an embodiment of a pre-filled syringe auto-injector 804 is configurable into a number of different configurations including a first, storage configuration for sterile storage of a pre-filled syringe, a second, alignment configuration for uncapping and alignment of the pre-filled syringe, and a third, injection configuration for injection of injectate into a subject.

The pre-filled syringe auto-injector 804 includes a housing 806 including a first housing section 808 that is slidably coupled to a second housing section 810. The first housing section 808 is sized and shaped to fit within the second housing section 810 such that the first housing section 808 and the second housing section 810 can slide relative to one another, in a telescoping manner, in a sliding direction 809. In other examples, the second housing section 810 is sized and shaped to fit within the first housing section 808 such that the first housing section 808 and the second housing section 810 can slide relative to one another, in a telescoping manner, in the sliding direction 809.

The first housing section 808 includes an injection opening 816 at its distal end 813. The distal end 813 of the first housing section 808 includes a removable seal 821 covering the injection opening 816 for preventing debris from entering the injection opening 816. During an injection operation, a needle of a syringe traverses the injection opening 816 and pierces a subject's skin. Injectate is injected into the subject via the needle of the syringe.

The housing 806 includes a syringe cap 824 coupled to the first housing section 808, a first energy storage element 826 coupled to the first housing section 808, a second energy storage element 827 with a distal end 829 coupled to the first housing section 808, and a syringe 828 pivotably coupled to a proximal end 811 of the second housing section 810.

In some examples, the first housing section 808 includes gripping features (e.g., snap-fit features) which interact with the syringe cap 824 to receive and retain the cap 824. The syringe cap 824 is configured to receive the distal end 832 of the syringe 828 to maintain sterility of the distal end 832 of the syringe 828.

The first energy storage element 826 (e.g., a spring or a flexure) is disposed between an outer surface of a sidewall 838 of the syringe 828 and an inner surface of a sidewall 840 of the second housing section 810. In some examples, the first energy storage element 826 applies a force to the outer surface of the sidewall 838 of the syringe 828 in a direction substantially perpendicular to the sliding direction 809.

The syringe 828 includes a needle 834 at its distal end 832, a syringe bore 842 for receiving injectate 844, and a flange 846 disposed at its proximal end 848. A stopper 850 is disposed in the syringe bore 842 and is configured to be moved along a length of the syringe 828 to force the injectate 844 out of the syringe 828 through the needle 834.

The second energy storage element 827 (e.g. a spring or flexure) extends from the first housing section 808 in a direction toward the proximal end 811 of the second housing section 810. At or near the proximal end 811 of the second housing section 810, the second energy storage element 827 curves such that it enters the syringe bore 842 and a proximal end 831 of the second energy storage element 827 makes contact with the stopper 850.

The proximal end 848 of the syringe 828 is pivotably held in place at the proximal end 811 of the second housing section 810 by an attachment member 852. In some examples, the attachment member 852 is a chamber that includes a through hole 856 with an inner diameter that is larger than an outer diameter of the main body 854 of the syringe 828 but is smaller than an outer diameter of the flange 846 of the syringe 828. With the syringe body 854 extending through the through hole 856, the flange 846 of the syringe 828 is held captive within the attachment member 852 due to the relatively larger outer diameter of the flange 846 preventing the flange 846 from passing through the through hole 856 which has a relatively smaller inner diameter.

The inner diameter of the through hole 856 is sufficiently large to allow the syringe 828 to move and pivot relative to the attachment member 852. The maximum range of movement and the maximum pivot angle is defined by dimensions of the syringe 828 (e.g., the outer diameters of the flange 846 and the main body 854) and the dimensions of the attachment member 852 (e.g., the inner diameter of the through hole 856). It is noted that the through hole 856 need not be a circular hole but can be of any sized and shape that pivotably holds the syringe 828 in place at the proximal end of the second housing section 810.

In other examples, the attachment member 852 includes snap-fit features for receiving and interacting with the flange 846 at the proximal end 848 of the syringe 828 to pivotably hold the syringe 828 in place. In yet other examples, the attachment member 852 is a partially enclosed chamber that is configured to receive a portion of the flange 846 at the proximal end 848 of the syringe 828 (e.g., the chamber can have a semi-circular shape configured to receive and pivotably hold half of the flange 846 at the proximal end 848 of the syringe 828).

3.1 Storage Configuration

In FIG. 8, the pre-filled syringe auto-injector 804 is shown in the first, storage configuration with the proximal end 848 of the syringe disposed in the attachment member 852. At least a portion of the flange 846 is engaged with an inner surface of the attachment member 852 such that the proximal end 848 of the syringe is contained within the attachment member 852.

The syringe 828 is pivoted such that it extends at an angle relative to the sliding direction 809 with its distal end 832 disposed in the syringe cap 824. The second energy storage element 827 is configured to hold the syringe 828 in the pivoted position with the distal end 832 of the syringe 828 disposed in the syringe cap 824.

3.2 Aligned Configuration

Figure 9:
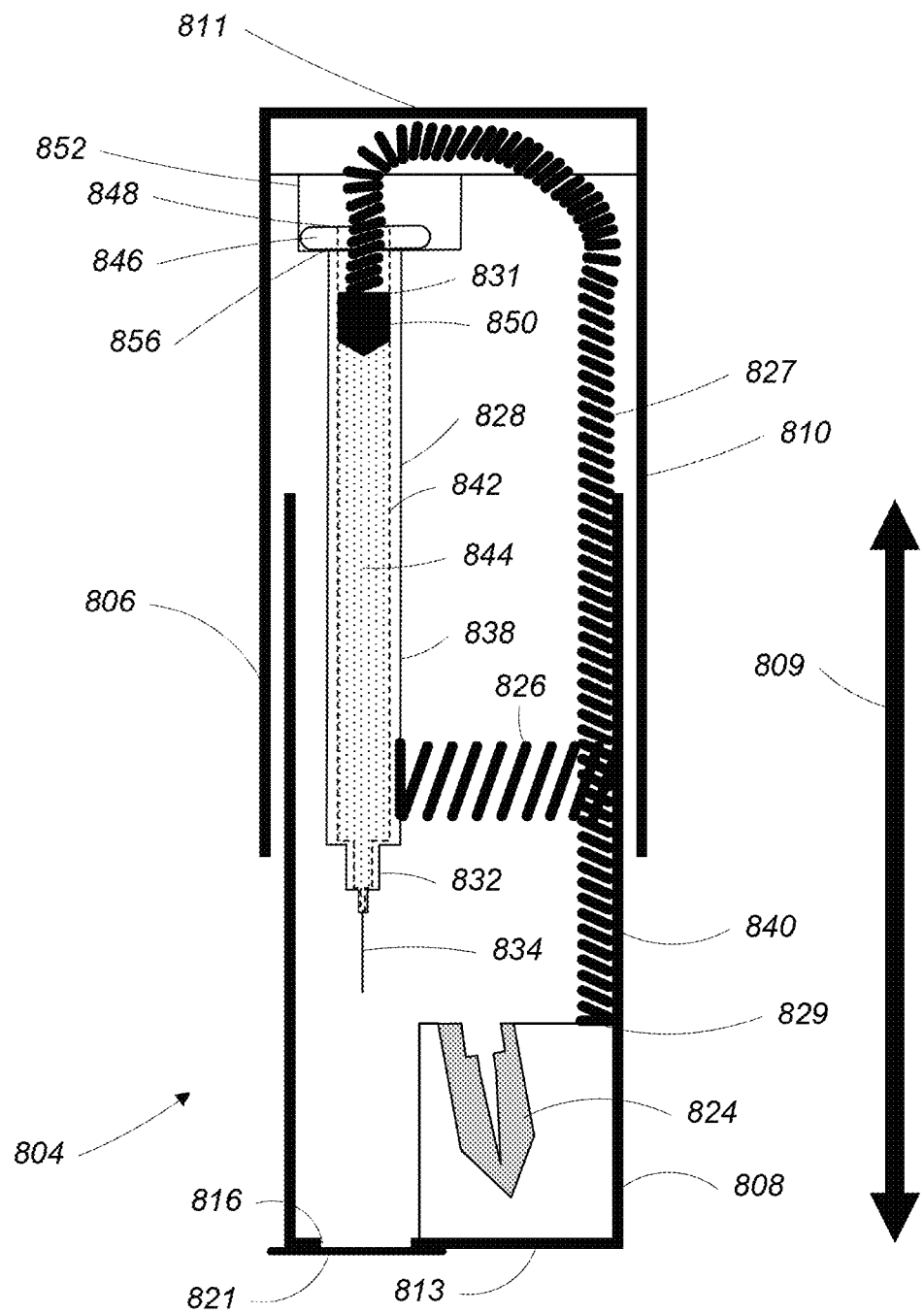
FIG. 9 is the pre-filled syringe auto-injector of FIG. 8 in an aligned configuration.

Referring to FIG. 9, to prepare for injection, the pre-filled syringe auto-injector 804 is moved to a second, aligned configuration. To move the pre-filled auto-injector 804 from the first, storage configuration to the second, aligned configuration, the first housing section 808 and the second housing section 810 are caused to move relative to one another in the sliding direction 809 such that the proximal end 811 of the second housing portion 810 is moved in a direction away from the distal end 813 of the first housing portion 808.

Since the syringe cap 824 is coupled to the first housing portion 808 and the syringe 828 is coupled to the second housing portion 810, the movement of the distal end 813 of the first housing portion 808 away from the proximal end 811 of the second housing portion 810 causes removal of the distal end 832 of the syringe 828 from the syringe cap 824. Once the needle 834 of the syringe 828 is fully removed from the syringe cap 824 (i.e., the needle 834 is clear of a proximal end 158 of the cap 824), the force applied to the outer surface of the sidewall 838 of the syringe 828 by the first energy storage element 826 causes the syringe 828 to pivot about the attachment member 852 such that the syringe 828 is brought into alignment with the injection opening 816 and extends substantially parallel to the sliding direction 809.

In some examples, the syringe 828 is maintained in the aligned configuration by the energy storage element 826 continuing to apply force to the outer surface of the sidewall 838 of the syringe 828 such that the syringe 826 is held between the energy storage element 826 and an outer surface of the injection chamber 818. In the aligned configuration, the second energy storage element 827 is elongated with its distal end 831 in contact with the syringe stopper 850.

3.3 Injection Configuration

Figure 10:
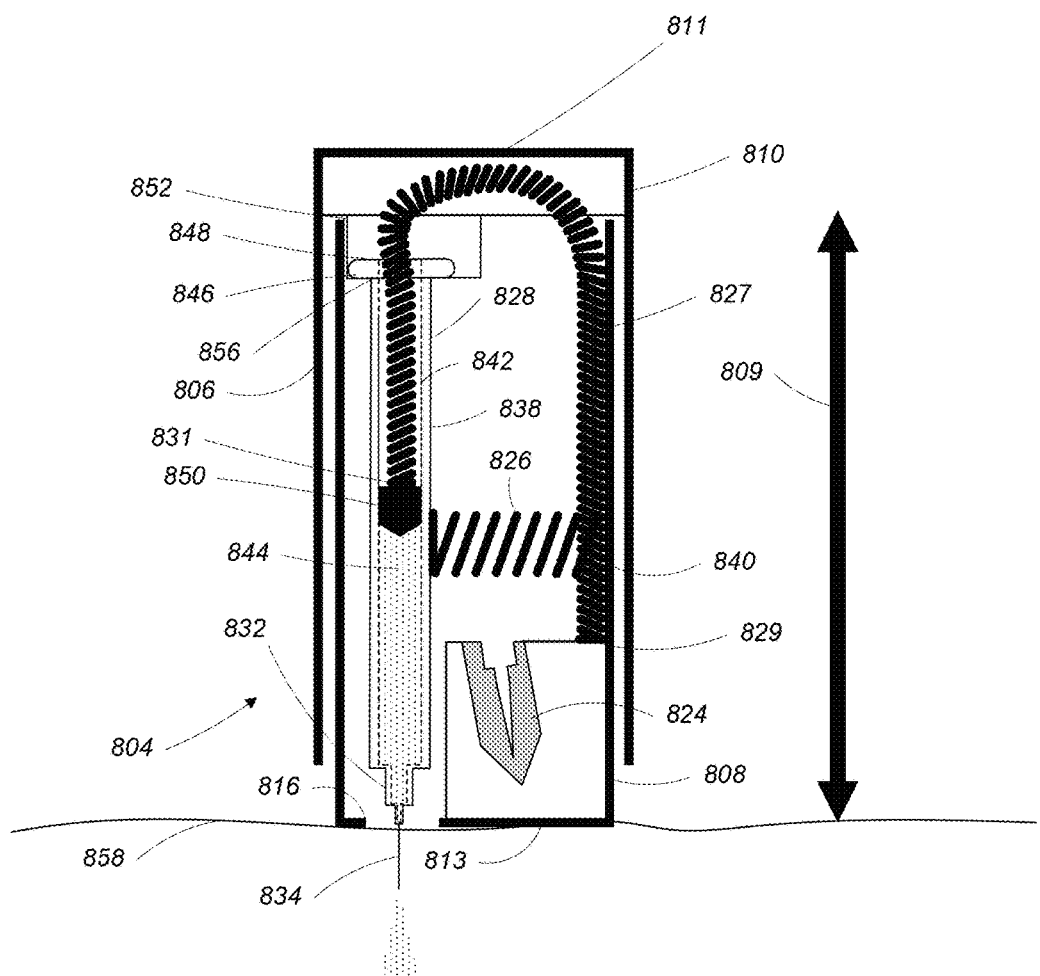
FIG. 10 is the pre-filled syringe auto-injector of FIG. 8 in an injection configuration.

Referring to FIG. 10, after the pre-filled syringe auto-injector 804 is moved to the second, aligned configuration, the pre-filled syringe auto-injector 804 is moved to the third, injection configuration. To move the pre-filled syringe auto-injector 804 from the second, aligned configuration to the third, injection configuration, the first housing section 808 and the second housing section 810 are caused to move relative to one another in the sliding direction 809 such that the proximal end 811 of the second housing section 810 is moved in a direction toward the distal end 813 of the first housing portion 808. As the first housing section 808 and the second housing section 810 move relative to one another, the distal end 811 of the second housing section 810 pushes on the second energy storage element 827, causing the syringe 828 to move in the sliding direction 809 toward the proximal end of the first housing section 808 until the distal end 832 of the syringe 828 traverses the injection opening 816 and pierces the subject's skin 845. As the first housing section 808 and the second housing section 810 continue move relative to one another, the distal end 811 of the second housing section 810 continues to push on the second energy storage element 827, forcing the second energy storage element 827 into the syringe bore 842 and moving the syringe plunger 850 in the sliding direction 809 such that the syringe plunger is moved in a direction toward the distal end 813 of the first housing portion 808. The movement of the syringe plunger 850 causes the injectate in the syringe bore 842 to be forced out of the injection bore 120 through the needle 834, and into the subject's body.

In some examples, the removable seal 821 is removed from the distal end 813 of the first housing portion 808 prior to moving the pre-filled syringe auto-injector 804 into the injection configuration. In other examples, the removable seal 821 is left on the distal end 813 of the first housing portion 808 and the needle 834 pierces the removable seal 821 when the pre-filled syringe auto-injector 804 is moved into the injection configuration.

4 Alternatives

In some examples, the pre-filled syringe fluid transfer injector cartridge 104 is operated between the storage, alignment, and fluid transfer configurations while detached from the injector mechanism 102. In other examples, the pre-filled syringe fluid transfer injector cartridge 104 is operated between the storage, alignment, and fluid transfer configurations while attached to the injector mechanism 102. In yet other examples, the pre-filled syringe fluid transfer injector cartridge 104 is operated between some of the storage, alignment, and fluid transfer configurations while detached from the injector mechanism 102 and other of the storage, alignment, and fluid transfer configurations while attached to the injector mechanism 102.

In some examples, the attachment member coupling the syringe to the second housing section includes a resilient member (e.g., a spring) which biases the syringe toward its position in the aligned configuration. In such examples, the energy storage element may or may not be included.

In some of the aspects described above, the syringe is inserted into the injector cartridge without a plunger rod attached to the syringe stopper. However, in some aspects, the syringe includes a plunger rod attached to the syringe stopper. In such aspects, the fluid transfer plunger interacts with the plunger rod during the fluid transfer phase rather than directly interacting with the syringe stopper and entering the syringe bore.

What is claimed is:

1. An injector cartridge for sterile storage and transfer of a fluid in a pre-filled syringe having a first end and a second end with a needle covered by a removable cap, the injector cartridge comprising:

an attachment member configured to pivotally constrain the first end of the pre-filled syringe;

a first housing section configured to axially retain the cap on the second end of the pre-filled syringe and including a syringe chamber configured to receive and axially retain the needle in a deployed position when the cap is removed from the second end;

a spring positioned to rotationally bias the second end of the pre-filled syringe from the cap toward the syringe chamber around a pivot formed at the attachment member;

the first housing section securing the cap and the syringe chamber in a fixed relationship to one another; and a second housing section coupled to the attachment member, the second housing section coupled in a sliding relationship to the first housing section, wherein, when the pre-filled syringe is placed between the attachment member and the first housing section, the syringe is decapped by the first housing section and rotated by the spring into alignment with the syringe chamber upon a first linear displacement of the second housing section away from the first housing section, and wherein the needle of the syringe is inserted into the syringe chamber by a subsequent linear displacement of the second housing section toward the first housing section.

2. The injector cartridge of claim 1 further comprising a fluid dispensing chamber, where the deployed position fluidly couples the pre-filled syringe to the fluid dispensing chamber.

3. The injector cartridge of claim 2 further comprising a channel extending between the syringe chamber and the fluid dispensing chamber for fluidly coupling the fluid dispensing chamber and the pre-filled syringe.

4. The injector cartridge of claim 3 wherein the channel includes a bung and the bung is punctured by the needle of the pre-filled syringe such that the pre-filled syringe and the fluid dispensing chamber are coupled.

5. The injector cartridge of claim 1 wherein the first housing section and the second housing section are configured to slide relative to each other.

6. The injector cartridge of claim 2 further comprising:
a nozzle disposed in a first wall at a distal end of the first housing section, the nozzle being in fluid communication with the fluid dispensing chamber;
a first opening disposed in a second wall at a proximal end of the second housing section and coaxially aligned with the fluid dispensing chamber; and
a second opening disposed in the second wall.

7. The injector cartridge of claim 6 further comprising the pre-filled syringe, wherein the pre-filled syringe includes a syringe bore which, in the deployed position of the syringe, extends in a direction such that the syringe bore is coaxially aligned with the second opening.

8. The injector cartridge of claim 6 further comprising a removable seal covering the nozzle.

9. An injector cartridge comprising:
a first section;
a second section slidably coupled to the first section permitting sliding of the second section in a sliding direction relative to the first section;
wherein the injector cartridge is configured to receive an elongated liquid-filled capsule having a first end and a second end opposite the first end, such that the capsule is pivotably coupled at the first end to the second section and mechanically biased to align the capsule with the sliding direction, and having an opening at the second end; and
wherein the injector cartridge is configured such that sliding the second section relative to the first section causes the injector cartridge to transform from a first configuration to a second configuration, and then sliding the first section relative to the second section causes the injector cartridge to transform from the second configuration to a third configuration different than the first configuration, and
in the first configuration of the injector cartridge, the injector cartridge causes the capsule to be angularly offset in direction from the sliding direction, and the second end of the capsule to be engaged in the first section of the housing such that the opening at the second end of the capsule is closed,
in the second configuration of the injector cartridge, the injector cartridge causes the capsule to be aligned with the sliding direction and the second end of the capsule to be free of the first section, and
in the third configuration of the injector cartridge, the injector cartridge causes the capsule to be aligned with the sliding direction and the second end of the capsule to be engaged in the first section such that the opening at the second end of the capsule permits transfer of fluid from the capsule.

10. The injector cartridge of claim 9 wherein the second section includes an energy storage element configured to be disposed between an inner surface of the second section and an outer surface of the capsule, the energy storage element being configured to provide the mechanical bias that aligns the capsule with the sliding direction.

11. The injector cartridge of claim 10 wherein the energy storage element includes a spring.

12. The injector cartridge of claim 11 wherein the spring has a first degree of compression in the first configuration and has a second degree of compression, less than the first degree of compression, in the second configuration and the third configuration.

13. The injector cartridge of claim 9 wherein the first section includes a cap and the injector cartridge is configured to cause the second end of the capsule to be disposed in the cap in the first configuration, and to be removed from the cap in the second configuration and the third configuration.

14. The injector cartridge of claim 9 further comprising a fluid transfer apparatus and a chamber including a chamber bore extending in a direction substantially parallel to the sliding direction, the fluid transfer apparatus including a fluid transfer channel in fluid communication with the chamber bore, the fluid transfer channel having a bung disposed therein.

15. The injector cartridge of claim 14 wherein, in the third configuration, the injector cartridge is configured to cause a portion of the second end of the capsule to extend through the bung and establish fluid communication between the capsule and the fluid transfer channel.

16. The injector cartridge of claim 14 further comprising
a nozzle disposed in a first wall at a distal end of the first section of the housing, the nozzle being in fluid communication with the chamber bore;
a first opening disposed in a second wall at a proximal end of the second section of the housing and coaxially aligned with the chamber bore; and
a second opening disposed in the second wall.

17. The injector cartridge of claim 16 further comprising the capsule, wherein the capsule includes a capsule bore which, in the third configuration, extends in a direction substantially parallel to the sliding direction such that the capsule bore is coaxially aligned with the second opening.

18. The injector cartridge of claim 9 wherein the second section includes a chamber for pivotably coupling the first end of the capsule to the second section, the chamber being configured to receive and contain a flange disposed at the first end of the capsule and including an opening configured to receive an elongate body of the capsule with the elongate body extending through the opening in the chamber.

19. The injector cartridge of claim 18 wherein the attachment member is formed as a snap-fit connection configured to receive and contain the flange.

20. A method for preparing an injector cartridge for use, the injector cartridge having a first section, a second section slidably coupled to the first section permitting sliding of the second section in a sliding direction relative to the first section, and an elongated liquid-filled capsule having a first end a second end opposite the first end, the capsule pivotably coupled at the first end to the second section and mechanically biased to align the capsule with the sliding direction, and having an opening at the second end, the method comprising:

accepting the injector cartridge in a first configuration in which the capsule is angularly offset in direction from the sliding direction, and the second end of the capsule is engaged in the first section of the housing such that the opening at the second end of the capsule is closed;

sliding the second section relative to the first section to cause the injector cartridge to transform from the first configuration to a second configuration in which the capsule is aligned with the sliding direction and the second end of the capsule is free of the first section; and sliding the second section relative to the first section to cause the injector cartridge to transform from the second configuration to a third configuration different that the first configuration in which the capsule is aligned with the sliding direction and the second end of the capsule is engaged in the first section such that the opening at the second end of the capsule is open permitting transfer of fluid from the capsule.

\* \* \* \* \*

UNITED STATES PATENT AND TRADEMARK OFFICE
CERTIFICATE OF CORRECTION

PATENT NO. : 10,376,656 B2
APPLICATION NO. : 15/598653
DATED : August 13, 2019
INVENTOR(S) : Robert Dyer and Andrew Coats Page 1 of 1

It is certified that error appears in the above-identified patent and that said Letters Patent is hereby corrected as shown below:

In the Claims

Column 14, Line 1 should read:
section of the injector cartridge such that the opening at the Column 14, Line 47 should read:
section of the injector cartridge, the nozzle being in fluid com- Column 14, Line 50 should read:
of the second section of the injector cartridge and coaxially Column 14, Line 65 should read:
19. The injector cartridge of claim 18 wherein an attatch- Column 15, Line 14 should read:
is engaged in the first section of the injector cartridge such that Signed and Sealed this
Eleventh Day of February, 2020

Andrei Iancu
*Director of the United States Patent and Trademark Office*